US00PP32093P2

(12) United States Plant Patent
Hansen

(10) Patent No.: US PP32,093 P2
(45) Date of Patent: Aug. 18, 2020

(54) ***PHLOX* PLANT NAMED 'OPENING ACT ULTRAPINK'**

(50) Latin Name: ***Phlox* hybrid**
Varietal Denomination: Opening Act Ultrapink

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 16/602,784

(22) Filed: Nov. 26, 2019

(51) Int. Cl.
*A01H 6/70* (2018.01)
*A01H 5/02* (2018.01)

(52) U.S. Cl.
USPC ..... Plt./320

(58) Field of Classification Search
USPC ..... Plt./320
CPC ..... A01H 6/70; A01H 5/02
See application file for complete search history.

*Primary Examiner* — Annette H Para

(57) ABSTRACT

A new and unique hybrid cultivar of *Phlox* plant named Phlox 'Opening Act Ultrapink' multi-stemmed, medium height, upright, slowly-spreading habit with clean, medium-green, glossy, lanceolate leaves with exceptional powdery mildew resistance. Foliage is thick and leathery on stiff stems. Flowers are vibrant, florescent, rose-pink, produced on branched peduncles and nearly cover the top of the plant beginning early summer, about two weeks prior typical *Phlox paniculata* cultivars, continuing for about five weeks and reblooming through late summer. 'Opening Act Ultrapink' is especially suitable as a potted plant, for the garden, for attracting hummingbirds and butterflies, and for cut flower arrangements.

1 Drawing Sheet

Botanical classification: *Phlox* hybrid.
Variety denomination: 'Opening Act Ultrapink'.

STATEMENT REGARDING PRIOR DISCLOSURES UNDER 37 CFR 1.77(B)(6)

The first disclosure, in the form of a sale, was made by Walters Gardens, Inc. on Apr. 6, 2019 to Walla Walla Nursery Co. Previously, Walters Gardens, Inc. also published a website with a photograph and non-enabling description on Dec. 1, 2018. Subsequently, Walters Gardens, Inc. published their "Walters Gardens 19-20 Catalog" on May 29, 2019. Walters Gardens, Inc. obtained the new plant and all information relating thereto, from the inventor. No plants of *Phlox* 'Opening Act Ultrapink' have been sold, in this country or anywhere in the world, under this or any name, nor has any disclosure of the new plant been made more than one year prior the filing date of this application, and such sale or disclosure within one year was either derived directly or indirectly from the inventor.

BACKGROUND OF THE INVENTION

The present invention relates to a new and distinct hybrid cultivar of *Phlox* plant, known as *Phlox* 'Opening Act Ultrapink' and will be referred to hereafter by its cultivar name or the "new plant". The new plant was the result of a cross pollination of 'Amethyst Pearl' U.S. Plant Pat. No. 28,487 as the female or seed parent and *Phlox carolina* 'Lil' Cahaba' (not patented) as the male or pollen parent. The cross was performed by the inventor on Nov. 17, 2013 in the greenhouses at a wholesale perennial nursery in Zeeland, Mich., and seed was collected in the early winter of 2014. During the trial process the new plant was identified by the breeder code 14-24-2. 'Opening Act Ultrapink' has been asexually propagated by tip and basal stem cuttings in the greenhouses at the same nursery in Zeeland, Mich. since 2016, as well as by shoot tip tissue culture. The unique characteristics of the new plant have been found to be reproducible and stable in successive generations of asexually propagated plants and the resultant plants have been found to be identical to the original selection.

BRIEF SUMMARY OF THE PLANT

*Phlox* 'Opening Act Ultrapink' is unique from its parents and all other tall garden *phlox* or other hybrid *Phlox* known to the inventor. The new plant differs from the female parent, 'Amethyst Pearl', in that the female parent is shorter and has light amethyst-pink-colored flowers. The male parent, 'Lil' Cahaba' is slightly taller and has flowers of pinky-mauve without the lighter face surrounding the darker eye. The closest comparison cultivars known to the inventor are *Phlox* 'Opening Act Pink-a-Dot' U.S. Plant Pat. No. 31,732, 'Cloudburst' U.S. Plant Pat. No. 30,289, 'Kung Fuchsia' U.S. Plant Pat. No. 31,308, 'Baby Doll Pink' U.S. Plant Patent Application copending; 'Opening Act Blush' U.S. Plant Pat. No. 27,462, 'Forever Pink' U.S. Plant Pat. No. 24,918, 'Fashionably Early Flamingo' U.S. Plant Pat. No. 29,911 and 'Fashionably Early Princess' U.S. Plant Pat. No. 28,680. 'Opening Act Pink-a-Dot' has similar habit with flowers that are near-white with a central star pattern of dark pink. 'Cloudburst' is slightly taller in habit and has more lavender purple flowers with smaller bright pink eyes. 'Kung Fuchsia' U.S. Plant patent application Ser. No. 16/501,030 is slightly shorter in habit and has bright fuchsia flower faces with light pink eye zones markings. 'Baby Doll Pink' has a shorter habit with flowers of darker pink and a white eye. 'Opening Act Blush' has a slightly shorter habit with smaller, light lavender-pink flowers. 'Forever Pink' has a shorter flower season smaller, dark pink flowers, and the habit is shorter. 'Fashionably Early Flamingo' has taller and broader habit with larger foliage and larger inflorescence and the flowers are light lavender-pink. 'Fashionably Early Princess' has flowers of light fuchsia-pink with a darker eye on slightly taller plants. 'Opening Act Ultrapink' differs from all other *phlox* known to the inventor in the following repeatedly observed traits in combination:

1. Plants of medium height, upright habit, slowly spreading by short rhizomes, producing clean, leathery, glossy, medium-green, lanceolate leaves;
2. Showing exceptional powdery mildew resistance;
3. Multiple branched, stems produce branched mounds of flowers starting early in the season;
4. Flower on strong stiff stems of about 72.0 cm tall producing vibrant, florescent, rose-pink flower;
5. Flowers cover nearly the entire top of the plant;
6. Flowering beginning in early-summer about two weeks prior to typical *Phlox paniculata* cultivars and re-blooming through late-summer.

BRIEF DESCRIPTION OF THE DRAWINGS

The photographs of the new plant demonstrate the unique traits of 'Opening Act Ultrapink' and the overall appearance of three-year-old plants grown in a full sun trial garden in Zeeland, Mich. The colors are as accurate as reasonably possible with color reproductions. Variation in ambient light spectrum, source and direction may cause the appearance of minor variation in color.

DETAILED BOTANICAL DESCRIPTION

Figure 1:
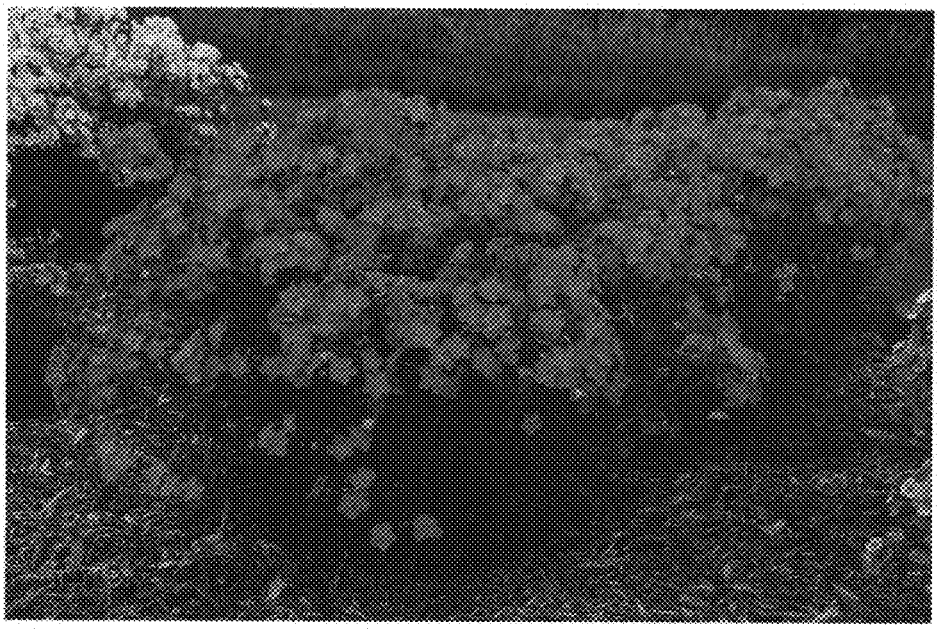
FIG. 1 shows the new plant in peak flower in the landscape.
Figure 2:
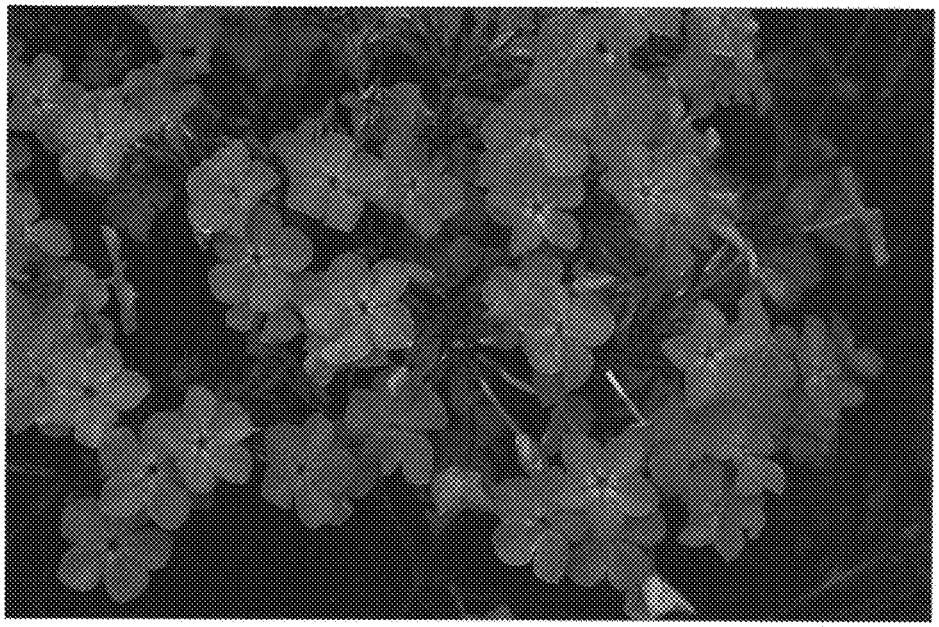
FIG. 2 shows a close-up of the floriferous flower head with flowers and buds.

The following descriptions and color references are based on the 2015 edition of The Royal Horticultural Society Colour Chart except where common dictionary terms are used. *Phlox* 'Opening Act Ultrapink' has not been observed under all possible environments. The phenotype may vary slightly with different growing environments such as temperature, light, fertility, soil pH, moisture and maturity levels, but without any change in the genotype. The following observations and size descriptions are based on three-year-old plants in the full sun garden of a wholesale perennial nursery in Zeeland, Mich. with supplemental fertilizer and water as needed.

Botanical classification: *Phlox* hybrid;

Parentage: Female or seed parent 'Amethyst Pearl' male or pollen parent *Phlox carolina* 'Lil' Cahaba';

Plant habit: Hardy herbaceous perennial, densely upright, producing about 30 rigid mostly upright stems; flowering about 72.0 cm tall and about 80.0 cm wide; flowering begins early summer in Michigan and continuing for about 5 weeks with repeating into late summer;

Propagation: Stem cuttings; rooting in about 14 days;

Time to produce finished crop in 3.8 liter pots: About 8 to 10 weeks; moderate rate of growth;

Root: Primary roots to about 1.0 mm thick; secondary fibrous and freely branching; color creamy white to tan depending on soil type;

Leaves: Simple, opposite, narrowly lanceolate; narrowly acute apex; rounded to truncate base; entire margin with micro-ciliolate in basal margin portion; tough, coriaceous;

Leaf size: To about 17.0 cm long by about 25.0 mm wide, average about 13.1 cm long by about 20.0 mm wide; becoming shorter and broader distally;

Leaf surfaces: Glabrous and lustrous adaxial and glabrous and matte adaxial;

Leaf color expanding: Adaxial between RHS N144D and RHS 144A, abaxial nearest RHS N144D;

Leaf color at flowering: Adaxial nearest RHS 137B, abaxial nearest RHS 146C;

Foliage fragrance: None detected;

Veins: Pinnate; glabrous adaxial and abaxial; midrib about 1.5 mm wide at base, slightly sunken adaxial and raised abaxial;

Vein color: Adaxial nearest RHS 146C and nearest RHS 160D on midrib, abaxial basal 5.0 mm nearest RHS 160B and distally nearest RHS 146C;

Petiole: Leaves sessile or to about 3.0 mm long and 3.0 mm across; concavo-convex; glabrous;

Petiole color (when present): Nearest RHS 146C;

Stems: About 64 per plant; terete; stiff; wiry; strong; mostly upright; glabrous; to about 72.0 cm, average about 66.0 cm long and 4.0 mm diameter at base;

Stem color: Nearest blend of RHS 145A and RHS 146D;

Nodes: About ten per stem below initial flowers; average internode length about 5.5 cm;

Node color: Nearest RHS 145A;

Inflorescence: A loosely-branched compound corymb of about 45 flowers; initial flowering portion about 14.0 cm long and 12.0 cm across;

Flowers: Perfect; salverform with flat face and long fused tube; actinomophic; typically with five petals; about 26.0 mm long total with tube about 25.0 mm long and 2.5 mm diameter; face about 30.0 mm across; attitude upright to slightly outward; self-cleaning;

Flower longevity: Individually about 5 days on plant or as cut flower;

Flower fragrance: Lightly sweet;

Buds one to two days prior to opening: Narrowly oblanceolate, to nearly clavate; acute apex with petals implicate about each other; base fused; total bud about 33.0 mm long, tube about 21.0 mm long and 2.5 mm diameter in tube, bulb 12.0 mm long and swollen to 4.0 mm diameter toward apex of convolute petals;

Bud color: Petals nearest RHS N81B in bulb and nearest RHS N79D in basal corolla tube and nearest RHS 79D in distal tube;

Petals: Five; margin entire; apex rounded; base fused into tube; abaxial and adaxial limb glabrous, abaxial tube surface glabrous, adaxial tube glabrous except pubescent with hairs nearest RHS NN155D in region about 4.0 mm from base; limbs imbricate about 20 percent over the next petal;

Petal size: Limb to about 12.0 mm wide and about 15.0 mm long, corolla tube to about 25.0 mm long and 2.5 mm diameter at face;

Petal color: (Young) adaxial limb nearest RHS NN78D with basal one-half of midrib nearest RHS NN78A; abaxial lighter than RHS NN78D and maculate with spots less than 0.2 mm diameter and nearest RHS NN78A; adaxial corolla tube basal 3.0 mm nearest RHS 150D, next distal 5.0 mm nearest RHS NN155C with distal one-half nearest RHS 72B; abaxial corolla tube basal 4.0 mm nearest RHS 150D, distally nearest RHS 77B with veins of nearest RHS 77A;

Petal color: (Mature) adaxial limb nearest blend between RHS NN78D and RHS 78D, adaxial corolla tube basal 3.0 mm nearest RHS 150D, next distal 5.0 mm nearest RHS NN155C with distal one-half nearest RHS 72B; abaxial limb nearest RHS N78D corolla tube nearest RHS 150D in basal 4.0 mm and distally nearest RHS 77B;

Androecium: Five;

*Filaments*.—Typically five; adnate to adaxial corolla tube except free in terminal 0.5 mm; varying lengths between 19.0 mm and 23.0 mm, less than 0.3 mm in diameter; color between RHS 72B and RHS 72C.

*Anther*.—Five; oblong elliptic; dorsifixed; longitudinal; about 3.5 mm long by 1.0 mm wide; color nearest RHS 13A.

*Pollen*.—Abundant; color nearest RHS 17B.

Gynoecium: One pistil per flower; to about 27.0 mm long;

*Style*.—Cylindrical; straight; about 24.0 mm long and about 0.3 mm diameter; persistent after flower abscission; color nearest RHS 145A.

*Stigma*.—Bifid in the distal 1.0 mm, about 0.3 mm in diameter; color nearest RHS 11A.

*Ovary*.—Superior; conical; acute apex, base truncate; about 2.0 mm long and 1.0 mm diameter; color nearest RHS 145A.

Calyx: Tubular; connate to corolla tube; to about 9.0 mm long and 3.0 mm cross at apex;

Sepals: Five; lanceolate; narrowly acute apex, margin entire; base fused; abaxial surface matte and adaxial slightly lustrous; persistent; individually about 9.0 mm long and 1.2 mm wide; fused in basal 4.0 mm;

Sepal color: Adaxial nearest RHS 146B with variable blush depending on light exposure of RHS 59A or RHS 59B, margin nearest RHS NN155B with highlight blush nearest RHS 59A; abaxial nearest RHS 146B with margins nearest RHS NN155B and highlight blushing of nearest RHS 59A or RHS 59B;

Peduncle: Glabrous, stiff, strong, moderately lustrous, upright, cylindrical; average about 66.0 cm long and 3.0 mm diameter at base of flower branches and about 4.0 mm diameter near soil; branches to about 30.0 mm long and 2.5 mm diameter at base;

Peduncle color: Nearest blend of RHS 145A and RHS 146D;

Bracts: Subtending upper branches and flowers; lanceolate; ciliolate margin; acute apex; sessile truncate base; to about 3.5 cm long and 1.5 cm across at base; same colors as leaves;

Pedicel: Cylindrical; puberulent to micro-glandular; average about 6.0 mm long and 1.0 mm diameter;

Pedicel color: Nearest RHS 146D with moderate blush in heavy light exposure to nearest RHS N79A;

Fruit and seeds have not yet been observed.

Hardiness and culture: The new plant grows best with plenty of moisture and adequate drainage; hardy to at least from USDA zone 4 through 8.

Disease and pest resistance: *Phlox* 'Opening Act Ultrapink' demonstrated the excellent powdery mildew resistance caused by *Erysiphe cichoracearum* in the presence and under conditions of intense pressure that would normally show symptoms.

I claim:

1. A new and distinct cultivar of hybrid *Phlox* plant named *Phlox* 'Opening Act Ultrapink', as herein described and illustrated.

* * * * *